(12) United States Patent
Bronson et al.

(10) Patent No.: US 10,249,218 B2
(45) Date of Patent: Apr. 2, 2019

(54) TOURNIQUET WITH AUDIO INSTRUCTIONS

(71) Applicant: North American Rescue, LLC, Greer, SC (US)

(72) Inventors: Brent Bronson, Duncan, SC (US); Matt Cupelli, Greer, SC (US)

(73) Assignee: North American Rescue, LLC, Greer, SC (US)

( * ) Notice: Subject to any disclaimer, the term of this patent is extended or adjusted under 35 U.S.C. 154(b) by 302 days.

(21) Appl. No.: 15/220,236

(22) Filed: Jul. 26, 2016

(65) Prior Publication Data

US 2017/0032698 A1  Feb. 2, 2017

Related U.S. Application Data

(60) Provisional application No. 62/197,164, filed on Jul. 27, 2015.

(51) Int. Cl.
| | |
|---|---|
| *G09B 23/28* | (2006.01) |
| *A61B 34/00* | (2016.01) |
| *A61B 90/00* | (2016.01) |
| *A61B 17/132* | (2006.01) |
| *G09B 5/04* | (2006.01) |
| *A61B 17/00* | (2006.01) |

(52) U.S. Cl.
CPC .......... *G09B 23/28* (2013.01); *A61B 17/1325* (2013.01); *A61B 34/25* (2016.02); *A61B 90/06* (2016.02); *G09B 5/04* (2013.01); *A61B 2017/00725* (2013.01); *A61B 2090/065* (2016.02)

(58) Field of Classification Search
CPC ............ A61B 17/1327; A61B 17/1322; A61B 17/1325; A61B 2090/065; G06F 19/00; G09B 23/28; G09B 5/04
See application file for complete search history.

(56) References Cited

U.S. PATENT DOCUMENTS

| | | | |
|---|---|---|---|
| 7,842,067 B2 | 11/2010 | Esposito | |
| 7,892,253 B2 | 2/2011 | Esposito | |
| 8,047,850 B2 | 11/2011 | Esposito | |
| 8,888,807 B2 | 11/2014 | Esposito | |
| 2006/0178865 A1 | 8/2006 | Edwards | |
| 2011/0123971 A1 | 5/2011 | Berkowitz | |
| 2011/0247963 A1* | 10/2011 | Stockett | G09B 23/288 206/572 |
| 2012/0116794 A1 | 5/2012 | Wilkerson-Amendell | |
| 2012/0252367 A1 | 10/2012 | Gaglio | |
| 2015/0044653 A1* | 2/2015 | Levine | G09B 7/08 434/262 |

(Continued)

*Primary Examiner* — Jerry-Daryl Fletcher
(74) *Attorney, Agent, or Firm* — Dority & Manning, P.A.

(57) ABSTRACT

A tourniquet with audio instructions comprising: a tourniquet with a belt, clip, securing strap, and instruction module; a release switch can be activated when the tourniquet is put in use so that audio instructions are provided to the user for using the tourniquet. The invention can include the instruction module being carried by a holster that also carries the tourniquet. The instruction module can be activated when the tourniquet is removed from the holster, unfolded or manually actuated. The tourniquet can be retained in a holster and the instruction module is activated when the tourniquet is removed from the holster.

20 Claims, 8 Drawing Sheets

(56) References Cited

U.S. PATENT DOCUMENTS

2016/0022277 A1* 1/2016 Eikman .............. A61B 17/1322
606/203
2016/0184148 A1* 6/2016 Johnson ................. A61F 17/00
206/570

* cited by examiner

TOURNIQUET WITH AUDIO INSTRUCTIONS

BACKGROUND OF THE INVENTION

1) Field of the Invention

The present invention relates to a medical device with audio instructions and more specifically a tourniquet with audio instructions to provide to the user operational instructions.

2) Description of Related Art

Tourniquets are designed to control life-threatening vascular hemorrhaging from extremity wounds. Improperly used, the tourniquet can create complications when improperly applied that can result in significant tissue damage, limb loss, increased bleeding, and increased mortality. From recent studies of the battlefield, it has been discovered that exsanguination from extremity wounds is the leading cause of preventable death among casualties in the battlefield. Particularly, tourniquets such as the Combat Application Tourniquet (C-A-T) (U.S. Pat. Nos. 7,842,067; 7,892,253; 8,047,850 and 8,888,807) have proven to be effective to reduce preventable combat deaths. Currently, the C-A-T is standard military issue and all soldiers are trained to use them.

Such tourniquets, including the C-A-T, has transitioned to civilian emergency care. Some police and fire departments routinely use them in the field, and were even crucial for emergency treatment of victims either at the location of the incident of subsequent health treatment locations.

When using the C-A-T, it has been shown to be fairly intuitive and even comes with printed instructions. However, medical professionals stress that for proper application to control bleeding and to avoid ischemic and neurological complications, proper use is critical. For both adults and children, the tourniquet should be placed just above the wound (such as 2 to 3 inches) and not just on the thigh or upper arm. The time of the tourniquet application should be recorded so that it can be provided to the medical professional. Under some medical guidelines, if the transportation time from the incident location to emergency care is less than two hours, the tourniquet can remain in place. However, when the transit time is longer (and the patient is stable), it may that in some cases the tourniquet would be gradually loosened and convert to hemostatic and/or pressure dressings to control the hemorrhaging. Following these, and other instructions, is critical as noted by medical professionals.

Tourniquets can be vitally important for wounds such as penetrating trauma from firearms and stabbings, terrorist incidents with high-velocity blast injuries to the limbs, injuries in rural or wilderness areas where resources are limited and transport to definitive care may be difficult or delayed, and industrial or farm accidents. In addressing the first two situations, there is a movement to provide such tourniquets as the C-A-T in public places such as airports, movie theaters, schools, malls, and the like. The challenge then becomes educating the general public on how to properly apply a tourniquet.

When the automated external defibrillators (AED) were initially placed in public, providing instructions for use was, in one format, through audio instructions such as United States Patent applications 2006/0178865. This AED naturally lends itself to audio instructions as it is an electronic device and its operating involves actuating the device, usually with a button. Therefore, it is natural to initiate the instructions through the push of a button. The use of recorded speech with medical devices has been used for attachment to medical devices such as United States Patent Application 2012/0252367 which include a port or a connector for interchangeably connecting the module to the medical device. United States Patent Application 2012/0116794 discloses a medical advice card and label containing an embedded audio chip or card. The embedded audio chip or card plays information related to a health care treatment plan in order to improve compliance with physician instructions. The medical advice card or label may also contain written information relating to the audible information related to a health care treatment plan. A similar device to provide for medical instructions is disclosed in United States Patent Application 2011/0123971. However, none of these references disclose an apparatus that is well suited for a tourniquet in that the tourniquet does not have the ability to be interfaced electronically with the audio device, applied under battlefield and emergency trauma environments, and can be easily separated from a cord.

Further, for the proper use of a field tourniquet, there are advantageous pressure ranges. The minimum effective pressure for a tourniquet applied to the thigh is 90 mm to 100 mm Hg above systolic blood pressure so that in a normotensive and non-obese injured individual, a pressure of 250 mm HG is sufficient. For tourniquet application to an arm, 200 mm Hg pressure is recommended.

Accordingly, it is an object of the present invention to provide for an instructional module for providing audio instructions directed to the proper application of a tourniquet.

It is another object of the present invention to provide for an instructional module that can be attached to a tourniquet.

It is another object of the present invention to provide for an instructional module that can be actuated in the normal operation of the tourniquet.

It is another object of the present invention to provide for information to an user concerning the proper pressure applied by the tourniquet.

SUMMARY OF THE INVENTION

The above objectives are accomplished according to the present invention by providing a tourniquet with audio instructions comprising: a tourniquet with a belt, clip, securing strap, and instruction module; a switch that is activated when the tourniquet is put in use so that audio instructions are provided to the user for using the tourniquet. The instruction module can be attached to the tourniquet, a holster that receives the tourniquet, can be removably attached to the tourniquet or the holster.

The invention can include a tourniquet having audio instructions comprising: a tourniquet with a belt and buckle removably carried by a tourniquet holster; an instruction module carried by the belt having a control module; a control medium included in the control module; an audio medium included in the control module having audio information stored on the audio medium configured to be broadcast through a speaker included in the information module; a manual switch included in the control module connected to the control medium that, when actuated, causes the audio information to be broadcast through the speaker; a release switch included in the control module connected to the control medium that, when actuated, causes the audio information to be broadcast through the speaker; a set of electrical contacts carried by the belt and connected to the control module configured to detect the perimeter of the belt when applied to an extremity; a strain gauge in communication with the control module configured to determine the compression force of the belt when applied to an extremity; and, a pressure indicator included in the control module that is actuated when the compression force falls below a predetermined level according to the perimeter of the belt.

The instruction module can be releasably carried by the belt configured to actuate the control module when the instructions module is removed from the belt. The instruction module can be releasably attached to a clip attached to the belt. A removable tab can be included in the release switch that when removed from the control module, actuates the control module. The tab can be is attached to a clip configured to release from the instruction module; and, the instruction module is configured to release from the tourniquet thereby removing the tab from the control module thereby actuating the control module. The tab can be attached to the belt toward a distal end of the belt relative to the buckle; and, the tab is received in the control module when the belt is in a folded position and removed from the control module when unfolded thereby actuating the control module.

The pressure indicator can be actuated by the control module when the control module detects the perimeter of the belt is less than seventeen inches and the compression force falls below 380 mm Hg. The pressure indicator can be actuated by the control module when the control module detects the perimeter of the belt is equal to or greater than seventeen inches and the compression force is falls below 280 mm Hg. The instruction module can be is releasably attached to the holster and configured to actuate control module to broadcast audio information when the tourniquet is removed from the holster.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Figure 1:
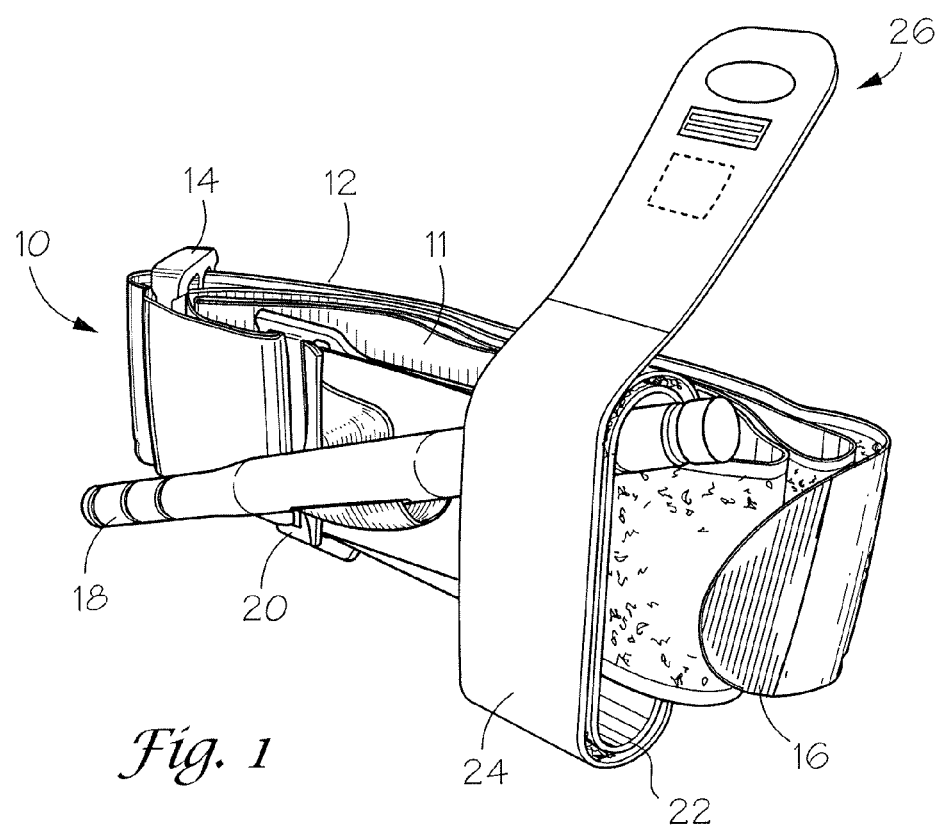
FIG. 1 is a perspective view of aspects of the invention.

Referring to FIG. 1, a tourniquet can include a belt 12 having a buckle 14 which receives a strap end 16 allowing the belt to encircle a limb. The belt can include a hook and loop fastener so that when the belt encircles the limb, the hook and loop fastener prevents the belt from slipping and therefore maintains the application diameter. A windless 18 can be included that can tighten the belt of an interior belt 20 to apply circumvential pressure or compression pressure to the limb. A clip 22 can be included to receive the windless so that when the windless is turned to apply pressure to the limb, the windless can be received in the clip to prevent the windless from turning and therefore maintain the pressure to the limb. A securing strap 24 can be carried by the clip and can be placed in a closed position securing the windless in the clip and an open position allowing the windless to be received into and removed from the clip. The securing strap can be attached to the clip by hook and loop fastener. The securing strap can include a "TIME:" marking to indicate to a user to record the time the tourniquet was applied.

Figure 2:
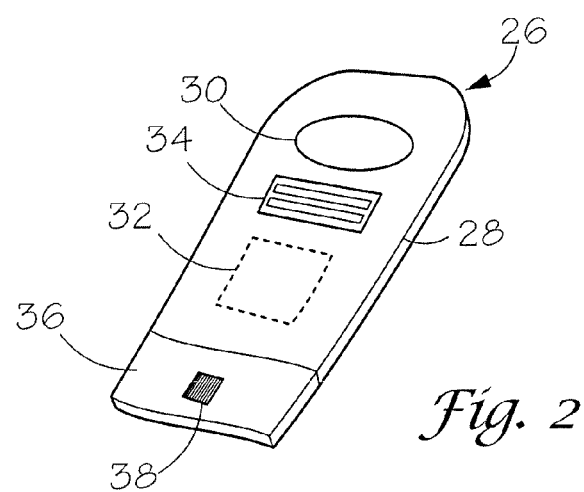
FIG. 2 is a perspective view of aspects of the invention.

Referring to FIGS. 1 and 2, an instruction module 26 can be attached or removably attached to the tourniquet. The instruction module can be carried by the belt by being attached to the belt, removablely attached to the belt, attached to a rigid portion or rigid plate 11 included in the tourniquet, attached to a holster that can receive the tourniquet, attached to the clip, or otherwise carried the belt. In one embodiment, the instruction module includes hook and loop fasteners so that the instruction module can be secured between the clip and securing strap. The instruction module can include a housing 28 which can be rigid, semi-rigid or flexible. A button 30 can be included to actuate the control module 32 manually to turn on and turnoff the audio instructions. The button can be disposed so that it extends through the housing or can be contained within the housing and actuated through the housing with external pressure. The control module can be contained within the housing. Speaker 34 can be carried by the housing to broadcast instructions on the use of the tourniquet.

The housing can include hook and loop fasteners 36 allowing the instruction module to be secured to the tourniquet between the securing strap and the clip. In one embodiment, the tourniquet is initially provided to the user with the securing strap in the closed position. When the securing strap is removed from the instruction module, a release switch 38 is actuated and the control module begins playing instructional audio. Therefore, the user is provided with the audio instructions when the tourniquet is put in use.

Figure 3:
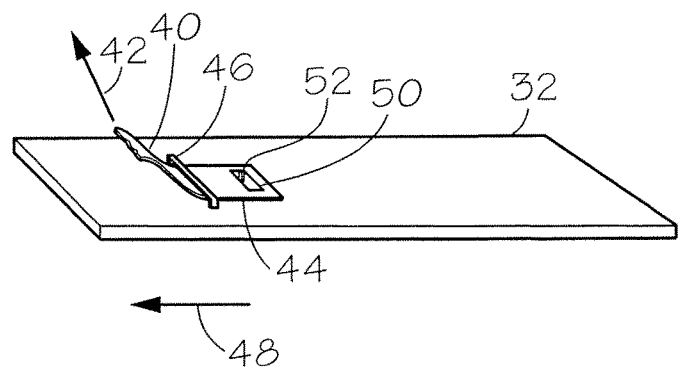
FIG. 3 is a perspective view of aspects of the invention.

Referring to FIG. 3, one component of the control module 32 can be seen. The control module can include a tab 40 that can be pulled when the securing strap is released from the instruction module. The tab can move in a direction shown as 42. When the tab is pulled, the direction of the pulling force is applied to a runner 44 and as the runner passes under a bridge 46, the runner is pulled in a direction shown as 48. The runner can include a contact area 50 that contacts pin 52 creating an electrical circuit causing the control module to play the audio instructions. Once the control module is caused to play the audio instructions, the audio instructions can play once, for a predetermined number of times, for a predetermined amount of time, until the tab is released and the contact between the pin and contact area is broken or until the power supply of the control module is exhausted.

Figure 4:
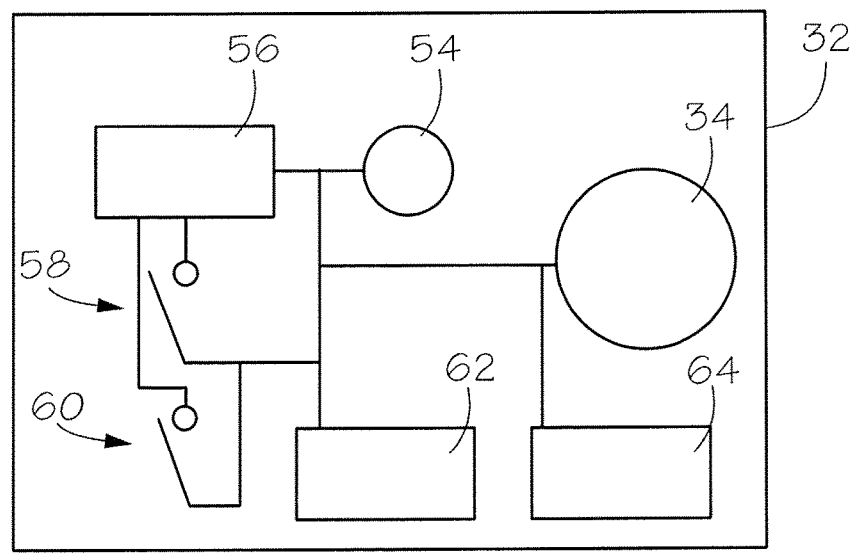
FIG. 4 is a plan view of aspects of the invention.

Referring FIG. 4, the control module 32 can include a microphone 54, speaker 34, power supply 56, activation switch 58, recording button 60, an audio medium 62, and control medium 64. In one embodiment, the audio medium and control medium are taken from the group of computer readable medium, circuit board, RAM, ROM, removable recordable medium, or any combination. The audio medium and control medium can be embodied in the same medium such as computer readable medium, RAM or ROM. The microphone can be used to record the audio instructions or information on the audio medium. In one embodiment, the instructions are preloaded on the control medium and there is no need for the microphone or record button. Computer readable instructions can be included on the control medium to provide the functionality of the control module making it a special purpose computer system.

The computer readable instructions can receive input from the activation switch and upon the switch being activated, the audio instructions can be played and broadcast from the speaker. The computer readable instructions can also monitor the power supply and provide an audio indication that the power supply is low and should be replaced. The power supply can be integrated into the control module so that in the event of low power supply, the control module can be replaced.

Figure 5:
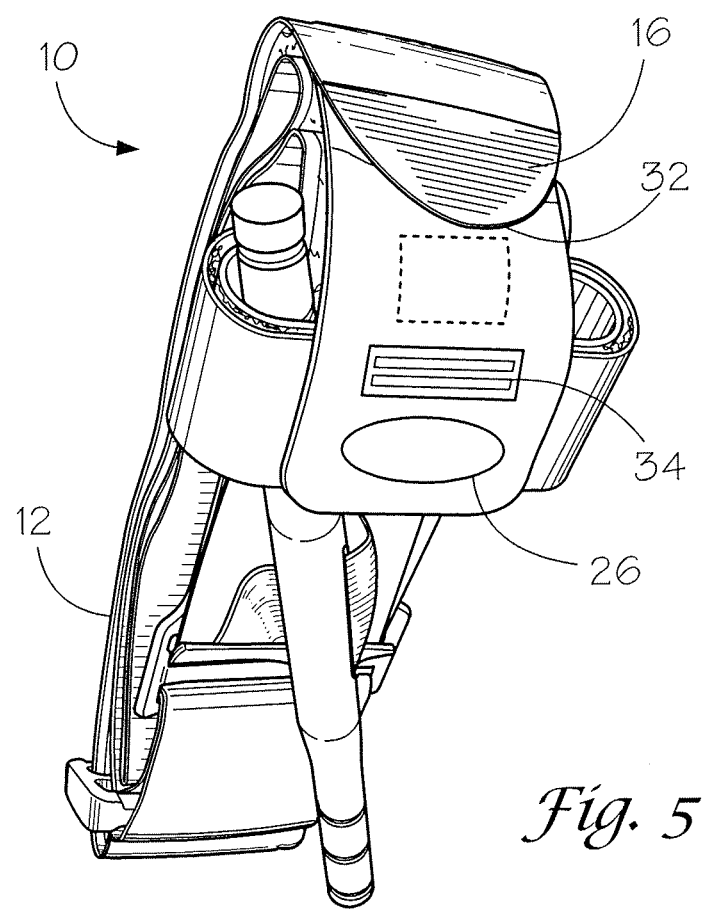
FIG. 5 is a perspective view of aspects of the invention.

Referring to FIG. 5, the instruction module 26 can be disposed between the strap end 16 and the belt 12, when the tourniquet is initially provided to the user. When the user removes the strap end from the belt, the instruction module is activated and the audio instructions are broadcast. The release switch can be removabley attached to the strap end of belt so that then the strap end is removed from the belt the release switch closes a circuit and the audio instructions are broadcast through speaker 34.

Figure 6:
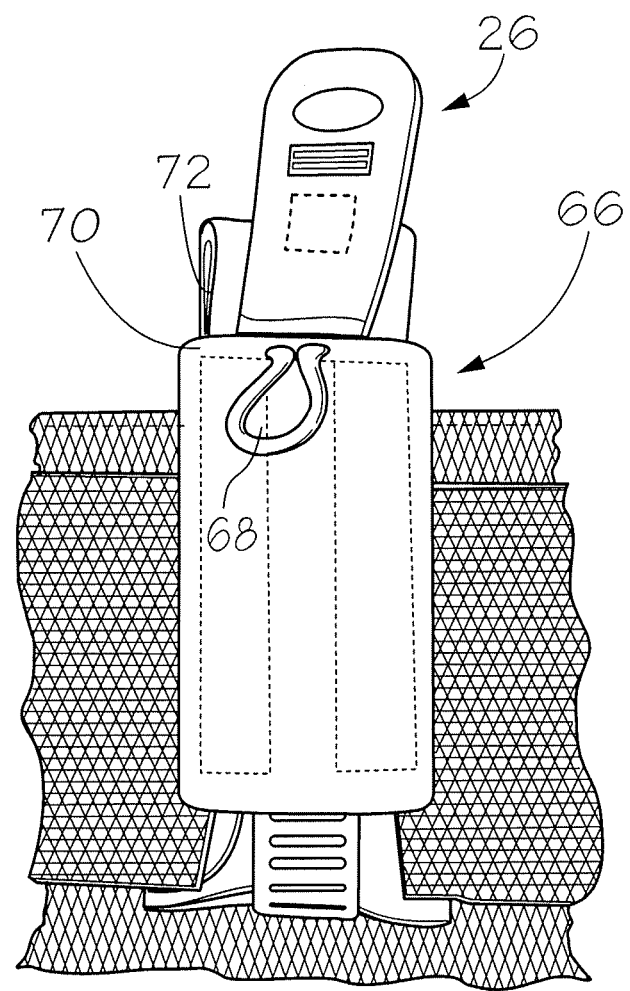
FIG. 6 is a front view of aspects of the invention.

Referring to FIG. 6, one embodiment is shown with a tourniquet holster 66 for receiving and securing a tourniquet. The tourniquet holster can be attached in a public location, mounted to a wall or other structure or fixture or removabley mounted to an object. The holster can include a pull tab 68 that can be used to release the tourniquet from the holster. When the pull tab is pulled downward, the front panel 70 can be released from the side and back panel of the holster and allow the tourniquet to be removed from the holster. The instruction module can be disposed between the front panel and a top cover 72 so that the instruction module 26 is activated when the pull tab is pulled.

Figure 7:
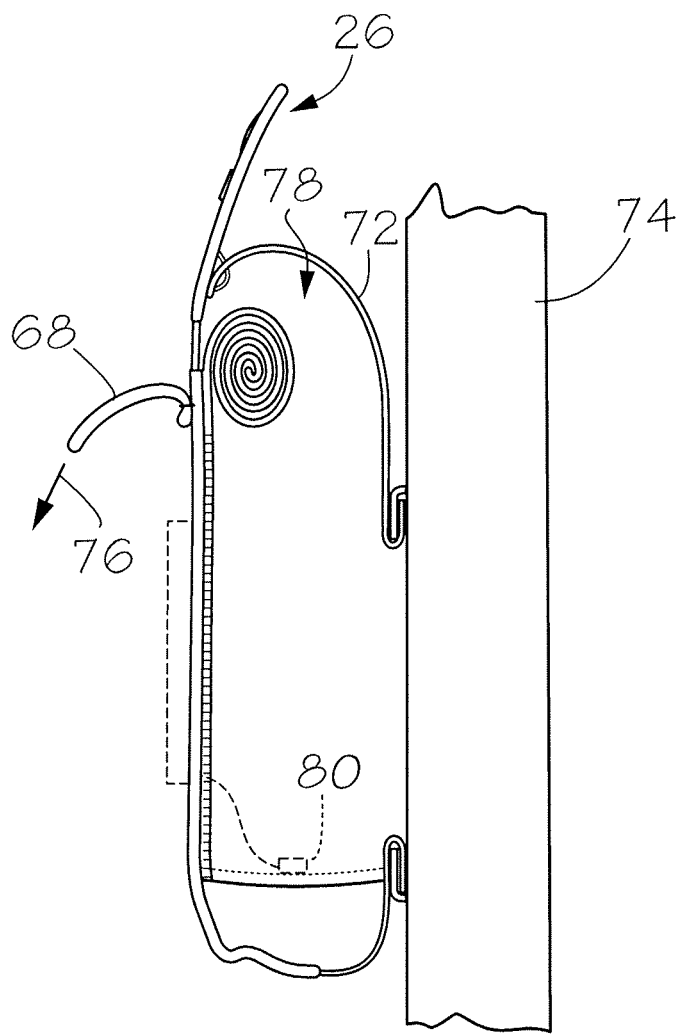
FIG. 7 is a side view of aspects of the invention.

Referring to FIG. 7, the tourniquet holster can be attached to a wall or other surface, including a vertical surface 74. When the pull tab 68 is pulled in a direction shown as 76, the instruction module 26 can be activated. The instruction module can also be activated when the tourniquet is removed from area 78 so that the tourniquet holster can be opened and closed without the information module activated. The tourniquet holster can be rigid, semi-flexible or flexible. The tourniquet holster can include the instruction module 26 attached to the holster and the instruction module when the tourniquet is removed from the holster through pressure switch or release switch 80.

Figure 8:
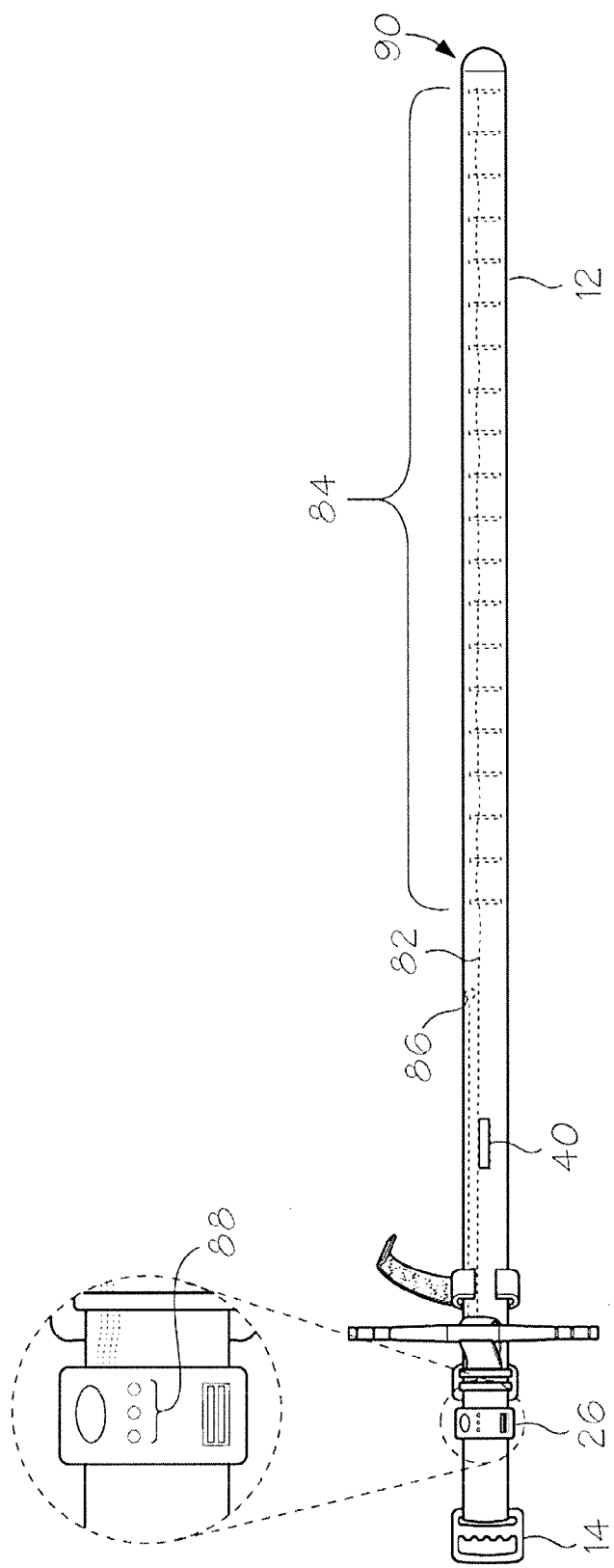
FIG. 8 is a top view of aspects of the invention.
Figure 9:
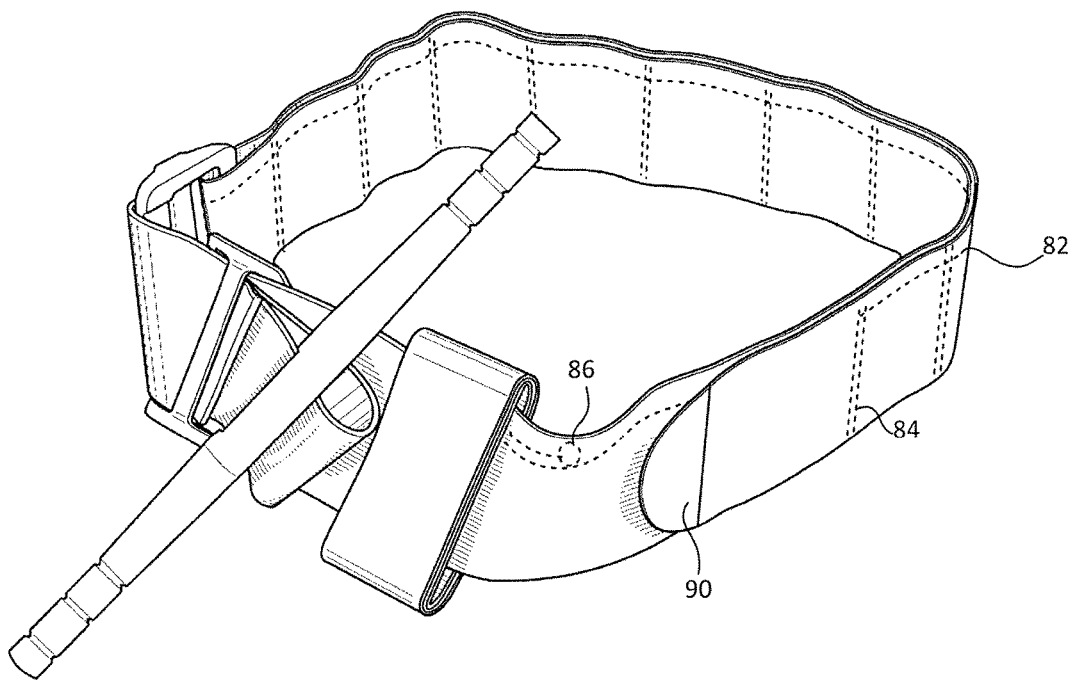
FIG. 9 is a perspective view of aspects of the invention; and,
FIG. 10 is side view of the invention in a folded configuration.

Referring to FIG. 8, one embodiment of the invention is shown with the belt extended. The instruction module can be carried by the belt and disposed near the buckle. In one embodiment, the instruction module is attached to a rigid plate that is attached to the belt. The instruction module can include an electrical connection 82 to a set of electrical contacts 84 carried by the belt. When the belt is inserted through the buckle and then attached to itself, as shown in FIG. 9, the electrical contacts of the overlapping portion of the belt can indicate the perimeter of the tourniquet when in use. In one embodiment, if the perimeter of the tourniquet prior to winding the windless is 17 inches or larger, it can be assumed that the tourniquet is wrapped around the thigh. If the perimeter of the tourniquet is less than 17 inches, it can be assumed that that the tourniquet is wrapper around the arm. The control module can use the determination of the perimeter to determine an range of tourniquet pressure that is within an acceptable range to occlude the blood supply preventing hemorrhaging from the extremity.

The control module can also include a gauge, strain gauge or other gauge or sensor 88 that can be attached to the belt so that when the belt is tightened around the extremity, the gauge measure the pressure being applied. The control module can include indicators 88 that can provide information visually such as turning red or flashing when there it too little pressure to sufficiently restrict blood flow. The control module can also cause audio information to be broadcast for communicating that the compression pressure of the belt is below a predetermined range. In one embodiment, the indicator can be actuated by the control module when the tourniquet is on a lower extremity and the applied pressure is lower than one of 220 mm Hg for normal systolic blood pressure, 260 mm Hg for high blood pressure, and 280 mm Hg for hypertensive care. For an upper extremity, the limits can be 320 mmHg, 360 mm Hg and 380 mm Hg respectively.

Figure 10:
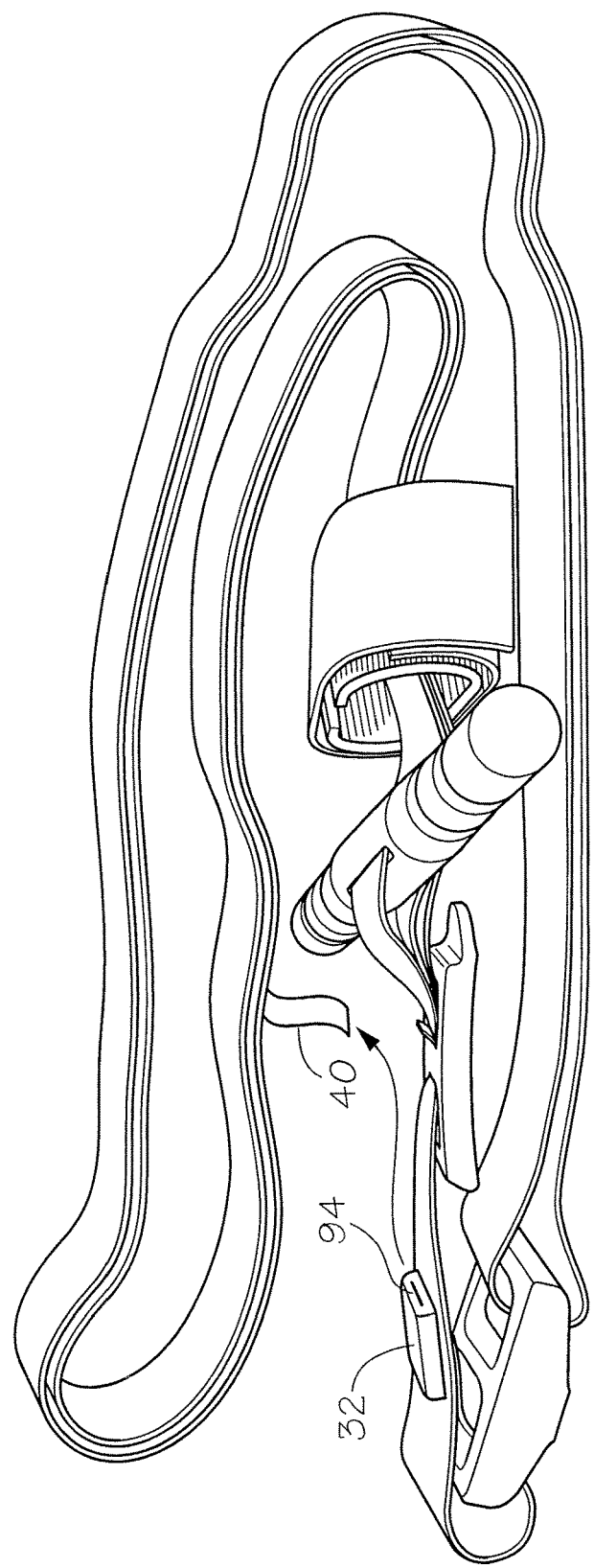

Referring to FIG. 10, tab 40 is shown attached to the belt at a position toward a distal end 90 (FIG. 8) relative to the buckle end 92. When in the folded position, the tab is inserted into the instruction or control module to open a circuit or prevent power to the control module. When the belt is unfolded, the tab is removed from the tab slot 94 and the control module is actuated. The tab, when removed, can actuate the control module. Therefore, the functionality of the control module, including the audio instructions, is actuated automatically upon unfolding the belt. In one embodiment, the tab is disposed in slot 94 and between to electrical contacts so that when the tab is removed, the electrical contacts actuate the control module or allows power to be applied to a circuit in the control module.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits, and advantages will be apparent from the above in conjunction with the accompanying examples, data, figures, and all reasonable inferences to be drawn therefrom, alone or with consideration of the references incorporated herein.

Unless specifically stated, terms, and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements, or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A tourniquet having audio instructions comprising:
a tourniquet with a belt and a buckle removably carried by a tourniquet holster;
an instruction module carried by the belt having a control module;
a control medium included in the control module;
an audio medium included in the control module having audio information stored on the audio medium representing tourniquet use instructions and configured to be broadcast through a speaker included in the instruction module;
a manual switch included in the control module connected to the control medium that, when actuated, causes the audio information to be broadcast through the speaker;
a release switch included in the control module connected to the control medium that, when actuated, causes the audio information to be broadcast through the speaker;
a set of electrical contacts carried by the belt and connected to the control module configured to detect a perimeter of the belt when applied to an extremity;
a gauge in communications with the control module configured to determine a compression force of the belt when applied to an extremity; and,
a pressure indicator included in the control module that is actuated when the compression force falls below a predetermined level.

2. The apparatus of claim 1 wherein the instruction module is releasably carried by the belt and configured to actuate the control module when the instructions module is removed from the belt.

3. The apparatus of claim 2 wherein the instruction module is releasably attached to a clip attached to the belt.

4. The apparatus of claim 1 including a removable tab included in the release switch that when removed from the control module, actuates the control module to broadcast audio information.

5. The apparatus of claim 4 including:
a clip carried by the belt;
the instruction module removably attached to the clip configured to release actuating the control module when removed from the clip.

6. The apparatus of claim 5 wherein:
the tab is attached to the belt toward a distal end of the belt relative to the buckle; and,
the tab is received in the control module when the belt is in a folded position and removed from the control module when the belt is unfolded thereby actuating the control module.

7. The apparatus of claim 1 wherein the pressure indicator is actuated by the control module when the control module detects the perimeter of the belt is less than seventeen inches and the compression force falls below 380 mm Hg.

8. The apparatus of claim 1 wherein pressure indicator is actuated by the control module when the control module detects the perimeter of the belt is equal to or greater than seventeen inches and the compression force is falls below 380 mm Hg.

9. The apparatus of claim 1 wherein the instruction module is releasably attached to the tourniquet holster and configured to actuate the control module to broadcast audio information when the tourniquet is removed from the holster.

10. A tourniquet having audio instructions comprising: a tourniquet with a belt and a buckle;
an instruction module carried by the belt having a control module; a control medium included in the control module;
an audio medium included in the control module having audio information configured to be broadcast through a speaker included in the instruction module;
a release switch included in the control module connected to the control medium that, when actuated, causes the audio information to be broadcast through the speaker;
a tab attached to the belt toward a distal end of the belt relative to the buckle; and, the tab is received in the control module when the belt is in a folded position and removed from the control module when the belt is unfolded thereby actuating the control module.

11. The apparatus of claim 10 including:
a gauge in communications with the control module configured to determine a compression force of the belt when applied to an extremity; and,
a pressure indicator actuated by the control module when the control module detects a perimeter of the belt is less than 380 mm Hg.

12. The apparatus of claim 11 including a set of electrical contacts carried by the belt and connected to the control module configured to detect the perimeter of the belt when applied to an extremity; and,
the pressure indicator actuated by the control module when the control module detects the perimeter is less than seventeen inches and the compression force is less than 280 mm Hg.

13. The apparatus of claim 11 including:
a set of electrical contacts carried by the belt and connected to the control module configured to detect the perimeter of the belt when applied to an extremity; and,
the pressure indicator actuated by the control module when the control module detects the perimeter is greater than or equal to seventeen inches and the compression force is less than 380 mm Hg.

14. The apparatus of claim 10 including a holster for receiving a tourniquet in a folded position.

15. The apparatus of claim 10 including a rigid plate attached to the belt and the instruction module.

16. The apparatus of claim 10 including a manual switch included in the control module connected to the control medium that, when actuated, causes the audio information to be broadcast.

17. A tourniquet having audio instructions comprising: a belt;
  an instruction module removably carried by the belt having a control module; a control medium included in the control module;
  an audio medium included in the control module having audio information stored on the audio medium configured to be broadcast through a speaker; and,
  a release switch included in the control module connected to the control medium configured to actuate the control module to broadcast the audio information through the speaker when the instruction module is removed from the belt.

18. The apparatus of claim 17 including a clip attached to the belt wherein the instruction module is removably attached to the clip.

19. The apparatus of claim 17 including:
  a gauge in communication with the control module configured to determine a compression force of the belt when applied to an extremity; and,
  a pressure indicator actuated by the control module when the control module detects the compression force is less than a predetermined level.

20. The apparatus of claim 19 including:
  a set of electrical contacts carried by the belt and connected to the control module configured to detect a perimeter of the belt when applied to an extremity; and,
  the pressure indicator actuated by the control module when the control module detects the perimeter is less than seventeen inches and the compression force is less than 380 mm Hg or when the perimeter is greater than or equal to seventeen inches and the compression force is less than 280 mm Hg.

* * * * *